United States Patent [19]
Huang et al.

[11] Patent Number: 6,083,421
[45] Date of Patent: Jul. 4, 2000

[54] FILM COATING COMPOSITION FOR WHITENING TEETH

[76] Inventors: Lizi Huang; Heming Xie, both of 4-3-2, Qindu Stomatology Hospital, Kangfu Road, Xian City, Shaanxi Province 710032, China

[21] Appl. No.: 09/101,827

[22] PCT Filed: Jan. 20, 1997

[86] PCT No.: PCT/CN97/00004

§ 371 Date: Sep. 17, 1998

§ 102(e) Date: Sep. 17, 1998

[87] PCT Pub. No.: WO97/25968

PCT Pub. Date: Jul. 24, 1997

[30] Foreign Application Priority Data

Jan. 19, 1996 [CN] China .................. 96 1 18605

[51] Int. Cl.[7] .............................. A01N 3/00; A01N 39/00; A61K 7/20
[52] U.S. Cl. ................... 252/186.28; 424/53; 424/613
[58] Field of Search ................ 424/53, 613; 252/186.28

[56] References Cited

U.S. PATENT DOCUMENTS

| | | |
|---|---|---|
| 4,032,627 | 6/1977 | Suchan et al. . |
| 5,171,564 | 12/1992 | Nathoo et al. . |
| 5,290,566 | 3/1994 | Schow et al. . |
| 5,425,953 | 6/1995 | Sintov et al. ........................ 424/404 |
| 5,785,957 | 7/1998 | Losee et al. ........................ 424/53 |
| 5,858,332 | 1/1999 | Jensen et al. ...................... 424/53 |
| 5,898,037 | 4/1999 | Marx ................................... 424/49 |

*Primary Examiner*—Cynthia Harris Kelly
*Assistant Examiner*—Monique T. Cole
*Attorney, Agent, or Firm*—Birch, Stewart, Kolasch & Birch, LLP

[57] ABSTRACT

The invention relates to a tooth-whitening varnish composition, comprising 6–20% of carbamide peroxide, 2–9% of film forming agent and 77–88% of volatile organic solvent, based on the total weight of the composition. The volatile organic solvent is selected from ether, ethylacetate, ethyl alcohol, or acetone. The film forming agent is artificial or natural material selected from cellulose, polyvinyl, butyral, coumarone resin or shellac. The composition can rapidly form films on dry tooth surfaces, and a remarkable tooth-whitening effect can be obtained.

5 Claims, No Drawings

FILM COATING COMPOSITION FOR WHITENING TEETH

This application is the national phase under 35 U.S.C. §371 of prior PCT International Application No. PCT/CN97/00004 which has an International filing date of Jan. 20, 1997 which designated the United States of America, the entire contents of which are hereby incorporated by reference.

TECHNICAL FIELD

This invention relates to tooth-whitening varnish composition.

BACKGROUND

With economic development and the improvement of living standard people pay more and more attention to white, clean, healthy tooth. Tooth can be pigmented due to various reasons in daily life. Dental fluorosis is caused by high level of fluoride in drinking water, tetracycline pigmented tooth is caused by excessive intake of tetracycline antibiotics during childhood. The other factors in daily life, for example, cigarette, tea, coffee, vinegar etc. can also pigment tooth. Thus tooth-bleaching and other cosmetic treatment has become a hot topic in dentistry.

Traditionally 33% oxygen peroxide was used to treat pigmented tooth. It is first applied to pigmented tooth surface, then the tooth is exposed to strong light, which can impel oxygen peroxide to decompose and release oxygen that have tooth-bleaching effects. But its application is limited because of its strong erosive effect. Haywood, an American dentist, et al, found in 1989 that carbamide peroxide can bleach tooth through releasing oxygen and its effective concentration of 10% has no erosive effect on gingiva. This finding was soon put to practical use and three generations of tooth-whitening products were produced. The first was 10% carbamide peroxide solution which could be used by dentist only. It was used by dipping some solution with a small cotton ball, then apply it to and maintain it on tooth surface for a period of time. Catalyzer, which can catalyze carbamide peroxide to decompose into water and carbamide and release oxygen, could be added at this time to enhance the reaction. The second was carbamide peroxide gel, the example product was Opalescence produced by an American company Ultradent. It was improved in its application method. A plastic denture was made according to the dental impression of the patient. The patient was asked to put the denture, with the gel in it, into mouth before going to bed and take it off in the morning. In this way, the reaction time of carbamide peroxide on tooth surface was extended. This was called "night tooth-bleaching technique". The improvement in the third generation was also its way of application. A specially-made soft tray, which fitted well with the patient's denture, was used to load tooth-bleaching agent. It was put into mouth for 1 hour every day, 7 days for a course of treatment. It usually took several treatment courses to see the effect.

It can be seen that the effectiveness of carbamide peroxide lies in the duration of its action on tooth surface. The above mentioned products used complicated appliances to extend its reaction time, which were complicate in operation and high in cost. An easy to use, low in cost tooth-whitening agent is badly needed at present.

OBJECT OF INVENTION

The object of this invention is to provide an easy to use, nontoxic, economical and strong effective tooth-whitening varnish composition.

SUMMARY OF INVENTION

The tooth-whitening varnish composition of the invention has carbamide peroxide as its active component. Through adding volatile organic solvent and film-forming agent to carbamide peroxide, a transparent and sticky composition is formed, which is easy to be applied to tooth surface and can form a film-like layer. Particularly, the composition comprises 6–20% of carbamide peroxide, 2–9% of film-forming agent and 77–88% of volatile organic solvent, based on the total weight of the composition. The volatile solvent is selected from ether, ethyl acetate, ethyl alcohol, acetone etc. The film-forming agent is of artificial or natural macromolecular material such as cellulose, polyvinyl butyarl, coumarone resin, shellac etc. Nontoxic fragrance, for example, jasmine oil, cinnamon oil can also be added to the composition. Colorant carmine, carthamin etc., which have no negative effect on whitening effect, is added mainly to indicate if this composition adheres to tooth surface.

With different content of carbamide peroxide the tooth-whitening varnish composition can be used both at home and under a doctor's guidance. When it is used at home, the content of carbamide peroxide is about 8–10% by weight of the composition. When it is used clinically, the concentration of it can be increased to 15–20% by weight of the composition. The low concentration of carbamide peroxide in home formula is to avoid gingival burn due to misuse of the composition.

The composition was prepared according to the following procedure: Put volatile organic solvent in a beaker, then place the beaker on a magnetic mixer. Gradually add filming-forming agent at 200 r/min and raise temperature to 40±5° C. Add ground carbamide peroxide after film-forming agent's complete dissolution. Continue with mixing until carbamide peroxide completely dissolve. Then cool down the solution to room temperature and the composition was obtained.

When this composition is used for tooth-whitening the only thing need to do is to dip some liquid composition with a little brush and apply it to dried tooth surface.

The composition can form a film on the tooth surface very quickly after application. Since the film adheres to tooth surface with certain mechanical intensity and chemical stability for more than an hour without peeling off or dissolution when there is no masticatory movements, carbamide peroxide, the active whitening component, can act directly on the tooth surface for a long time and obtain evident whitening effect. Compared with other bleaching products, it is easy to use and low in cost and can be used both in hospital and at home.

BEST MODE TO CARRY OUT THE INVENTION

The invention is further described with reference to the following example.

EXAMPLE 1

85 g ethyl acetate and 5 g coumarone resin were put in a beaker, then the beaker was placed on a magnetic mixer. The temperature was increased to 40° C. during the mixing process(200 r/min). After complete dissolution of resin 10 g of carbamide peroxide was added to the solution. Continue with mixing until carbamide peroxide completely dissolve. The solution was cooled down to room temperature, thus a transparent sticky composition was obtained.

EXAMPLE 2

The procedure was the same as that in Example 1, except that 83 g ethyl alcohol, 7 g polyvinyl butyral and 9 g carbamide peroxide were used.

EXAMPLE 3

The procedure was the same as that in Example 1, except that 80 g acetone, 5 g coumarone resin and 15 g carbamide peroxide respectively.

EXAMPLE 4

The procedure was the same as that in Example 1, except that 79 g ethyl acetate, 5 g shellac and 16 g carbamide peroxide were used.

EXAMPLE 5

The procedure was the same as that in Example 1, except that 79 g ethyl alcohol, 3 g polyvinyl butyral and 18 g carbamide peroxide were used.

EXAMPLE 6

The procedure was the same as that in Example 1, except that 80 g ethyl acetate, 7 g polyvinyl butyral and 13 g carbamide peroxide were used.

EXAMPLE 7

The procedure was the same as that in Example 1, except that 79 g ethyl acetate, 6 g shellac and 15 g carbamide peroxide were used.

EXAMPLE 8

The procedure was the same as that in Example 1, except that 80 g ethyl alcohol, 5 g coumarone resin and 15 g carbamide peroxide were used.

EXPERIMENTS

The following experiments were conducted in order to test the whitening effect and toxicity of the composition.

I. Acute Toxicity Test

Materials and methods: 40 Kunming albino mice (supplied by the Animal Center of the Fourth Military Medical University, FMMU), with half male and half female, weighing about 20 g, were used. A suspension of the tooth-whitening composition, with a concentration of 200 mg/ml, was prepared by diluting in 20 ml double distilled water 4 g of the ground film which was formed by dropping the composition onto the surface of a sterile petri dish.

The 40 mice were randomly divided into 4 groups, with 10 in each group. The suspension was given orally to each mouse in group 1 (10 g per kilogram weight) with a dose of 0.1 ml each time, once an hour for 10 times. In group 2, a total of 0.5 ml (5 g per kilogram weight) was given orally. In group 3, 0.2 ml suspension was given (2 g per kilogram weight). As for control group each mouse was given 1 ml of double distilled water (0.1 ml each time, once an hour for 10 times).

Results: The animals were observed for their behavior, hair, ingestion, urine and stool for 7 days after intake of the medicine. All mice were alive and no abnormalities were found. When the animals were dissected no abnormal changes were observed in heart, lung, liver, spleen and kidney. $LD_{50}$>5000 mg/kg weight. This composition is actual nontoxic grade according to oral acute toxicity criteria of the "standards of disinfect technique" by Chinese Association of Pharmacology, Branch of Toxity.

II. Tooth Lesion Test

Tooth lesion test was done according to the method of Haywood, V. B et al (Quintessence Int. 1990,21: 801–804). 20 freshly extracted teeth (supplied by Department of maxillofacial Surgery, college of Stomatology of FMMU) were divided at the middle of the crown in halves with a grit. Tooth-whitening varnish was applied to one half of the tooth crown randomly, the other half served as control. Then the specimens were prepared for scanning electron microscope observation in conventional method. The results showed that the control group tooth surface was badly contaminated while there was almost no foams on the tooth surface of the varnish group and no evident enamel lesion was observed.

III. Mucous Membrane Irritation Test

Tooth-whitening varnish suspension was prepared according to the procedure described in acute toxicity test with concentrations of 200 mg/ml and 100 mg/ml. Put the suspension in refrigerator for 48 hours for later use.

30 guinea pig (supplied by the Animal Center of the FMMU), with half male and half female, weighing about 250 g were used. The animals were randomly divided into 3 groups, with 10 in each group. In group 1 (large dose group), a drop of 200 mg/ml suspension was dripped to incisor gingiva and placed with a probe gently into gingival sulcus of the guinea pig. The procedure was repeated for 4 times, once in an hour. Observe the changes of local mucous membrane and general condition for 24 hours. Then put 2 of the animals to death and dissected the incisor and upper molar gingiva and their nearby membrane, pharyngeal and upper trachea membrane for histological observation under naked eye and light microscope. The remaining 8 were put to death on the $7^{th}$ day for observation.

The experiment methods in group 2 and group 3 were the same as in group 1 except that the concentration of the suspension was 100 mg/ml (small dose) in group 2 and double distilled water was used in group 3.

The oral mucous membrane and gingiva reaction score criteria were shown in table 1, which was made according to the conjunctiva irritation score criteria published by Chinese Association of Pharmacology, Branch of Toxicology

TABLE 1

Oral mucous membrane and gingiva reaction score criteria

| congestion, bleeding | score | edema, ulcer | score |
| --- | --- | --- | --- |
| blood vessel normal | 0 | no edema | 0 |
| blood vessel congested, bright red | 1 | slight edema | 1 |
| blood vessel congested, carmine | 2 | obvious edema | 2 |
| blood vessel congested, magenta | 3 | edema with | 4 |
| congestion with gingival tendency to bleed | 4 | gingival erosion, ulcer | |

$$\text{average reaction score} = \frac{\text{total score of congestion, bleeding} + \text{edema, ulcer}}{\text{total animal number}}$$

The results were given in table 2. The remaining 24 guinea pig were fed for 7 days to observe their behavior, hair, ingestion, urine and stool. No abnormalities were found. The membrane in experiment zone and other parts was normal under naked eye and microscopic observation after the animals were put to death. There was no difference between the two varnish suspension groups and control group.

TABLE 2

Average reaction score of oral mucous membrane and gingiva to tooth-whitening varnish

| group | number of animal | | time course average reaction score | | | | average reaction score | | | |
|---|---|---|---|---|---|---|---|---|---|---|
| | 24 h before | 24 h after | 1 h | 24 h | 48 h | 72 h | 1 h | 24 h | 48 h | 72 h |
| large dose | 10 | 8 | 2 | 1 | 0 | 0 | 0.2 | 0.1 | 0 | 0 |
| small dose | 10 | 8 | 0 | 0 | 0 | 0 | 0 | 0 | 0 | 0 |
| control | 10 | 8 | 0 | 0 | 0 | 0 | 0 | 0 | 0 | 0 |

IV. Skin Hypersensitive Test 30 guinea pigs(supplied by the Animal Center of FMMU), half male and half female, weighing about 230 g, were used in this experiments. The animals were randomly divided into 3 groups, with 10 in each group. 24 hours before the experiment, hair on both sides of the back of the animals were molted for an area of about 10 cm². A round shaped varnish composition film (5 mm in diameter and about 1 mm in thickness, prepared by putting the composition in a sterile petri dish in order to let the volatile solvent to evaporate and form a solid film on the plate) was adhered to the molted skin of left back and fixed there with a non irritating tape for 6 hours for each animal. The procedure was repeated at day 14. The animals in group 2(positive group) were subjected to 1.0% 2.4-dinitrochlorobenzene while the animals in group 3(control group) were subjected to 0.2 g double distilled water. On the $28^{th}$ day, a concentration of 0.1% 2.4-dinitrochlorobenzene (Provocative dose) was given to the molted skin on the right back of all animals. The area was then rinsed with normal saline and reaction results were observed instantly and at 24 hours, 48 hours and 72 hours respectively. Anaphylaxis level was decided according to the criteria in table 3.

TABLE 3

Skin anaphylaxis level score criteria

| skin erythema | score | skin edema | score |
|---|---|---|---|
| no erythema | 0 | no edema | 0 |
| slight erythema | 1 | slight edema | 1 |
| moderate erythema | 2 | moderate edema | 2 |
| severe erythema | 3 | severe edema | 3 |
| edematic erythema | 4 | | |

The results were given in Table 4. There was slight skin erythema on the tested area in positive group(anaphylaxis rate 100%). There was no skin erythema or edema in negative control group. The results in the composition group were the same as in control group.

TABLE 4

Results of skin hypersensitivity test

| group | number of animal | average time course reaction score | | | | precentage of sensitization (%) |
|---|---|---|---|---|---|---|
| | | 6 h | 24 h | 48 h | 72 h | |
| control group | 10 | 0 | 0 | 0 | 0 | 0 |
| varnish group | 10 | 0 | 0 | 0 | 0 | 0 |
| positive group | 10 | 1 | 1 | 0.8 | 0.5 | 100 |

Except the above experiments, the inventor has also followed up 168 patients (1667 teeth) who have used the varnish composition to see the effectiveness of the varnish. The results are shown in Table 5.

TABLE 5

Effects of tooth-whitening vanish

| group | patient number | tooth number | average application | complete whitening | | effective | | uneffective | |
|---|---|---|---|---|---|---|---|---|---|
| | | | | tooth number | % | tooth number | % | tooth number | % |
| cigarette, tea pigmented tooth | 83 | 901 | 5.4 | 896 | 99.45 | 5 | 5 55 | 0 | 0 |
| slight and mediate dental flurosis | 44 | 352 | 20.3 | 296 | 84.09 | 48 | 13.64 | 8 | 2.77 |
| slight tetracycline pigmented tooth | 41 | 414 | 36.5 | 322 | 77.78 | 12 | 2.89 | 80 | 19.33 |
| total | 168 | 1667 | 16.3 | 1514 | 90.82 | 65 | 3.90 | 88 | 5.28 |

It can be concluded that the tooth-whitening varnish composition is very effective in treating pigmented tooth. It is most effective to cigarette and tea pigmentation.

What is claimed is:

1. A nonaqueous tooth-whitening varnish composition comprising 6–20% of carbamide peroxide, characterized in that it further comprises 2–9% of film forming agent and 77–88% of volatile organic solvent, based on the total weight of the composition, wherein said film forming agent is selected from the group consisting of polyvinyl butyral, coumarone resin and shellac.

2. The composition as claimed in claim 1, wherein said volatile organic solvent is ether, ethylacetate, ethyl alcohol or acetone.

3. The composition as claimed in claim 1, further comprising fragrance and colorant which are suitable for human use.

4. The composition as claimed in claim 3, wherein said fragrance is jasmine oil or cinnammon oil.

5. The composition as claimed in claim 3, wherein said colorant is carmine or carthamin.

\* \* \* \* \*